(12) United States Patent
Kasama

(10) Patent No.: US 8,942,796 B2
(45) Date of Patent: Jan. 27, 2015

(54) EXERCISE DETERMINATION METHOD, AND ELECTRONIC DEVICE

(71) Applicant: Fujitsu Limited, Kawasaki-shi, Kanagawa (JP)

(72) Inventor: Kouichirou Kasama, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 0 days.

(21) Appl. No.: 13/923,913

(22) Filed: Jun. 21, 2013

(65) Prior Publication Data

US 2014/0052010 A1    Feb. 20, 2014

(30) Foreign Application Priority Data

Aug. 17, 2012   (JP) .................................. 2012-181044

(51) Int. Cl.
*A61B 5/04* (2006.01)
*A61B 5/024* (2006.01)
*A61B 5/11* (2006.01)
*A61B 5/00* (2006.01)

(52) U.S. Cl.
CPC .............. *A61B 5/024* (2013.01); *A61B 5/02416* (2013.01); *A61B 5/1118* (2013.01); *A61B 5/1123* (2013.01); *A61B 5/4866* (2013.01); *A61B 5/7207* (2013.01); *A61B 2503/10* (2013.01); *A61B 2503/12* (2013.01); *A61B 2560/0209* (2013.01)

USPC .......................................... 600/520; 600/508

(58) Field of Classification Search
USPC .................................................. 600/508, 520
See application file for complete search history.

(56) References Cited

U.S. PATENT DOCUMENTS

2012/0253485 A1* 10/2012 Weast et al. ..................... 700/91
2014/0125491 A1*  5/2014 Park et al. ................. 340/870.01

FOREIGN PATENT DOCUMENTS

| JP | 09-056705 A | 3/1997 |
| JP | 09-294727 A | 11/1997 |
| JP | 11-056827 A | 3/1999 |
| WO | WO 2009071128 A1 * | 6/2009 |

* cited by examiner

*Primary Examiner* — Christopher D Koharski
*Assistant Examiner* — Michael Carey
(74) *Attorney, Agent, or Firm* — Maschoff Brennan

(57) ABSTRACT

An exercise determination method includes: acquiring a detection value from an acceleration sensor; and controlling, by a processor, starting or stopping of a heart rate sensor depending on the acquired detection value. An electronic device includes a memory; and a processor coupled to the memory, configured to acquire a detection value from an acceleration sensor, and control starting or stopping of a heart rate sensor depending on the acquired detection value.

7 Claims, 16 Drawing Sheets

FIG. 3

| CHANGE DIFFERENTIAL VALUE OF ACCELERATION SENSOR VALUE (AVERAGE VALUE OF 20 SAMPLES) | ABSOLUTE VALUE OF CHANGE (DIFFERENTIAL VALUE) IN HEART RATE OF MILLIMETER WAVE SENSOR | SENSOR TO BE STARTED |
|---|---|---|
| LARGEST AMOUNT OF CHANGE (DIFFERENTIAL VALUE) AMONG THOSE OF THREE AXES IS LESS THAN 200 mG | NOT STARTED | ACCELERATION SENSOR |
| LARGEST AMOUNT OF CHANGE (DIFFERENTIAL VALUE) AMONG THOSE OF THREE AXES IS 200 mG OR MORE | NOT STARTED | MILLIMETER WAVE SENSOR |
| NOT STARTED | ABSOLUTE VALUE OF CHANGE (DIFFERENTIAL VALUE) IS LESS THAN 6 bpm | ACCELERATION SENSOR |
| NOT STARTED | ABSOLUTE VALUE OF CHANGE (DIFFERENTIAL VALUE) IS 6 bpm OR MORE | MILLIMETER WAVE SENSOR |

EXERCISE DETERMINATION METHOD, AND ELECTRONIC DEVICE

CROSS-REFERENCE TO RELATED APPLICATION

This application is based upon and claims the benefit of priority from the prior Japanese Patent Application No. 2012-181044 filed on Aug. 17, 2012, the entire contents of which are incorporated herein by reference.

FIELD

The embodiments discussed herein are related to an exercise determination method, an electronic device, and an exercise determination program.

BACKGROUND

In some portable terminals of recent years, an acceleration sensor and a heart rate sensor are incorporated. Regarding such a portable terminal, the function of measuring a subject's calorie consumption on the basis of accelerations along three axes detected by an acceleration sensor and the heart rate detected by a heart rate sensor is known. Thus, the subject is able to recognize his/her calorie consumption from a result of the measurement. Such a technology is disclosed in Japanese Laid-open Patent Publication No. 9-56705.

SUMMARY

According to an aspect of the invention, an exercise determination method includes: acquiring a detection value from an acceleration sensor; and controlling, by a processor, starting or stopping of a heart rate sensor depending on the acquired detection value.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 3 is an explanatory illustration of an example of a switching table of the first embodiment;

DESCRIPTION OF EMBODIMENTS

In existing techniques, the power consumption of the heart rate sensor is markedly high when compared to the acceleration sensor, for example. In the above portable terminal, the heart rate sensor as well as the acceleration sensor is operating at all times. Power consumption is therefore a serious issue for the portable terminal because a limitation is imposed on the amount of power that the portable terminal may consume. Besides, since the heart rate sensor is operating at all times, power is also consumed for processing that is performed based on a result of detection made by the heart rate sensor.

In one aspect of the present disclosure, the power consumption of a portable electronic device may be reduced.

Hereinafter, embodiments of an exercise determination program, a portable electronic device, an exercise determination method, and an information processing device disclosed in the present disclosure will be described in detail with reference to the drawings. It is to be noted that the disclosed technology is not limited to the present embodiment. Embodiments described below may be appropriately combined without causing a contradiction.

First Embodiment

Figure 1:
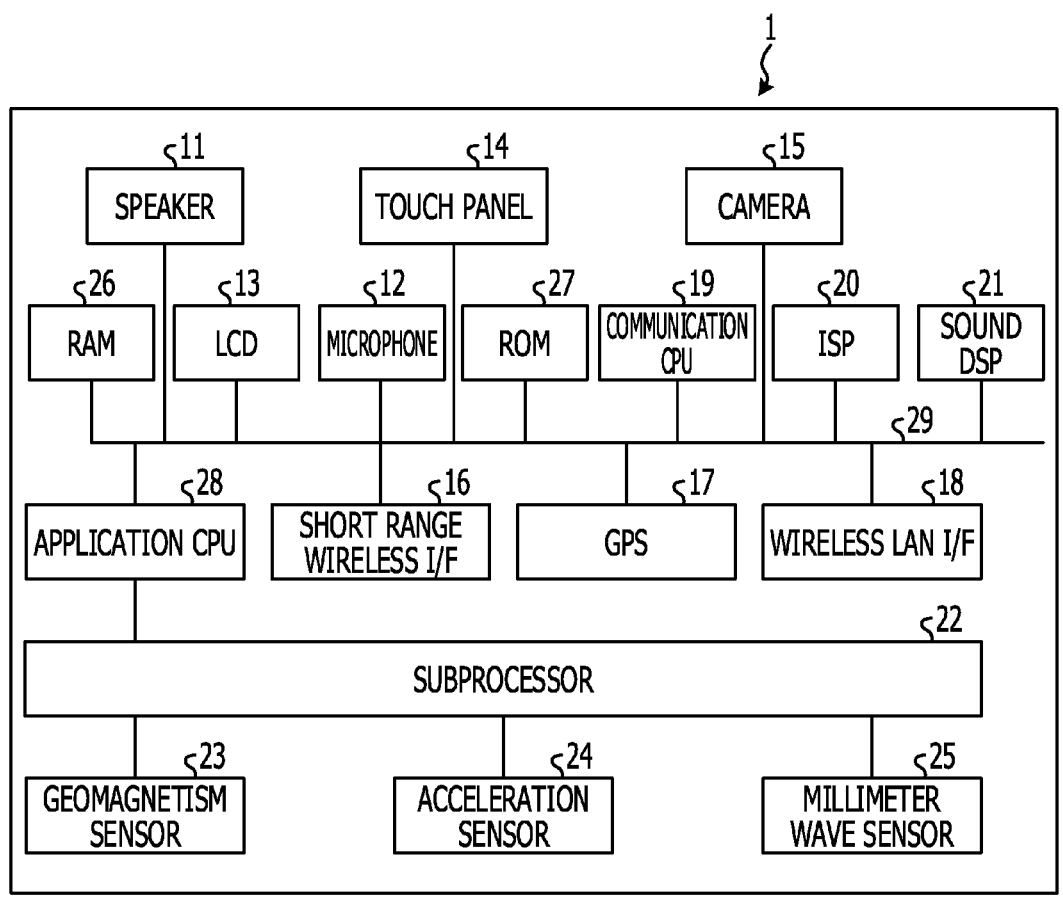
FIG. 1 is an explanatory diagram illustrating an example of a portable terminal of a first embodiment.

FIG. 1 is an explanatory diagram illustrating an example of a portable terminal 1 of a first embodiment. The portable terminal 1 illustrated in FIG. 1 is, for example, a portable telephone terminal, such as a smartphone. The portable terminal 1 includes a speaker 11, a microphone 12, a liquid crystal display (LCD) 13, a touch panel 14, a camera 15, a short-range wireless interface (hereinafter referred to simply as "I/F") 16, and a global positioning system (GPS) 17 unit. Additionally, the portable terminal 1 includes a wireless local area network (LAN) I/F 18, a communication central processing unit (CPU) 19, an imaging signal processor 20, a sound digital signal processor (DSP) 21, and a subprocessor 22.

Additionally, the portable terminal 1 includes a geomagnetism sensor 23, an acceleration sensor 24, a millimeter wave sensor 25, a random access memory (RAM) 26, a read only memory (ROM) 27, and an application CPU 28.

The LCD 13 displays various kinds of information. The touch panel 14 detects touch operations on the screen of the LCD 13. The short range wireless I/F 16 is an interface that handles a short range wireless communication function. The GPS unit 17 is part of a system that measures the current position of the portable terminal 1 using GPS satellites. The wireless LAN I/F 18 is an interface that handles a wireless LAN function. The communication CPU 19 is a CPU that handles various communication functions, such as a mobile phone communication function. The ISP 20 is a processor that handles image signal processing. The sound DSP 21 is a processor that handles speech signal processing. The subprocessor 22 is an external processor that executes a movement determination program, for example. The geomagnetism sensor 23 is a sensor that detects the orientation of the portable terminal 1, for example.

The acceleration sensor 24 is a sensor that detects the accelerations of the portable terminal 1 along the three axes of an x-axis, a y-axis, and a z-axis. The millimeter wave sensor 25 is an example of a heart rate sensor, and is a sensor that captures the Doppler shift of the state where the body surface of a subject varies (velocity) each time a heartbeat occurs, thereby detecting the heartbeat of the subject so as to measure the heart rate. This sensor may be a sensor that applies light of an LED to the inside of a living body and then measures the reflected light to detect heartbeats. Note that the subject is a user who possesses the portable terminal 1, for example. The ROM 27 is, for example, a nonvolatile memory that stores various programs, such as an exercise determination program. The RAM 26 is designed to store various kinds of information. The application CPU 28 controls the entirety of the portable terminal 1. A bus 29 interconnects various devices such as the application CPU 28 and the RAM 26 disposed inside the portable terminal 1.

Figure 2:
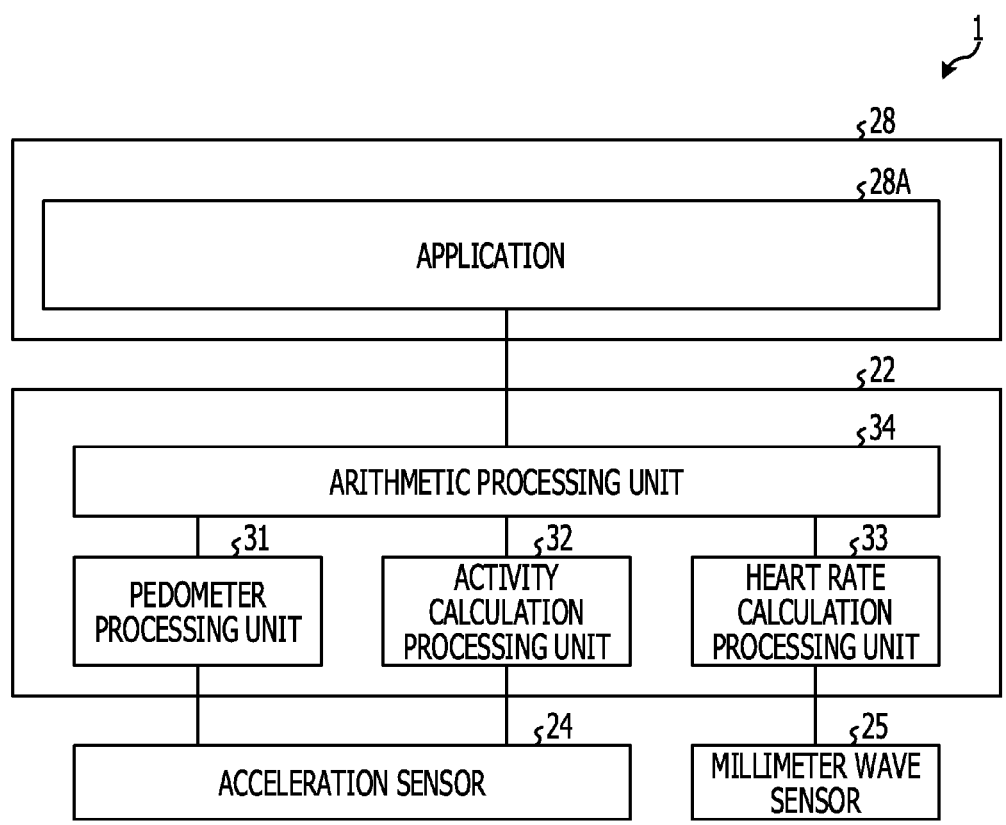
FIG. 2 is an explanatory diagram illustrating an example of a functional configuration of an application CPU and a subprocessor of the first embodiment.

FIG. 2 is an explanatory diagram illustrating an example of a functional configuration of the application CPU 28 and the subprocessor 22 of the first embodiment. Note that the subprocessor 22 and the application CPU 28 read an exercise determination program stored in the ROM 27, and construct various processes as functions on the basis of the read exercise determination program. The subprocessor 22 illustrated in FIG. 2 causes a pedometer processing unit 31, an activity calculation processing unit 32, a heart rate calculation processing unit 33, and an arithmetic processing unit 34 to operate as process functions. The pedometer processing unit 31 counts the number of steps on the basis of accelerations detected by the acceleration sensor 24, and calculates a walking speed based on the number of steps. Additionally, the pedometer processing unit 31 determines the exercise intensity corresponding to the walking speed based on the number of steps in a period equivalent to one minute, using a conversion table (not illustrated) of the exercise intensity corresponding to the walking speed.

Using an exercise intensity/exercise level calculation algorithm, the activity calculation processing unit 32 calculates the exercise intensity averaged for one second based on accelerations detected by the acceleration sensor 24. The heart rate calculation processing unit 33 calculates the maximum heart rate reserve on the basis of a heart rate detected by the millimeter wave sensor 25. Note that the maximum heart rate reserve γ is calculated using $(220-\alpha)-\beta$, where α is the age of a user and β is the heart rate at rest. Using a conversion table (not illustrated) of the exercise intensity corresponding to the proportion M (%) of the current heart rate in the maximum heart rate reserve γ, the heart rate calculation processing unit 33 calculates the exercise intensity averaged for one second.

The arithmetic processing unit 34 controls the start of the pedometer processing unit 31, activity calculation processing unit 32, and heart rate calculation processing unit 33. Additionally, by using the pedometer processing unit 31, the arithmetic processing unit 34 determines that a subject is in the walking state if less than 150 steps are taken in one minute, for example. Additionally, the arithmetic processing unit 34 determines that the subject is in the running state if 150 steps or more are taken in one minute, for example. Additionally, on the basis of the exercise intensities obtained by the pedometer processing unit 31, the activity calculation processing unit 32, and the heart rate calculation processing unit 33, the arithmetic processing unit 34 makes a determination as to whether the state of exercise of the subject is aerobic exercise. For example, the arithmetic processing unit 34 determines that the state of exercise of the subject is aerobic exercise if the current exercise intensity is within the range from 3.0 to 5.0 metabolic equivalents (METs), and determines that the state is not aerobic exercise if the current exercise intensity is outside the range of 3.0 to 5.0 METs. Additionally, on the basis of a result of detection made by the acceleration sensor 24 or the millimeter wave sensor 25, the arithmetic processing unit 34 makes a determination as to whether the walking state of the subject is in an excessive condition. At the time of changes in the state of exercise, the walking state of the subject is in the excessive condition where the variation in the state of exercise is large, which occurs at start of walking and so on, for example, and in a stationary condition where the variation in the state of exercise is small, which occurs during walking, for example. The application CPU 28 runs application software (hereinafter referred to simply as an "application") 28A for a determination of aerobic exercise, a determination of awakening, and so on, as functions, for example.

A switching table 40 illustrated in FIG. 3 is stored in the RAM 26. FIG. 3 is an explanatory illustration of an example of the switching table 40 of the first embodiment. The switching table 40 illustrated in FIG. 3 manages a change differential value 40A of the acceleration sensor value (change values of 20 samples), an absolute value 40B of change (differential value) in the heart rate of the millimeter wave sensor 25, and a sensor 40C to be started in association with one another. The change differential value 40A of the acceleration sensor value is an amount of change (differential value) that is a difference between the average of 20 samples for each of the x-axis acceleration, the y-axis acceleration, and the z-axis acceleration detected by the acceleration sensor 24, and the average of the previous 20 samples. Then, the change differential value 40A of the acceleration sensor value is compared with a threshold for a determination as to whether the walking state of the subject is in the excessive condition. With reference to the switching table 40, the arithmetic processing unit 34 determines that the walking state of the subject is in the stationary condition if the largest amount of change (differential value) among the amounts of change (differential value) of the three axes is less than the threshold, for example, 200 mG, and uses the acceleration sensor 24. Note that, when using the acceleration sensor 24, the arithmetic processing unit 34 stops the millimeter wave sensor 25. As a result, the power consumption of the millimeter wave sensor 25 may be reduced. With reference to the switching table 40, the arithmetic processing unit 34 also determines that the walking state of the subject is in the excessive condition if the largest amount of change (differential value) among the amounts of change (differential value) of the three axes is 200 mG or more, and starts the millimeter wave sensor 25. Note that, even when starting the millimeter wave sensor 25, the arithmetic processing unit 34 uses the acceleration sensor 24 for another application without stopping the acceleration sensor 24.

The absolute value 40B of a change (differential value) in the heart rate is the absolute value of the amount of change (differential value) that is a difference between the current heart rate measured during the past one minute (a period at the present time) and the previous heart rate for one minute measured during the previous one-minute period, and is used for a determination as to whether the walking state is in the excessive condition. With reference to the switching table 40, the arithmetic processing unit 34 determines that the walking state of the subject is in the stationary condition if the absolute value of the amount of change (differential value) in heart rate is less than a threshold, for example, 6 beats per minute (bpm), and uses the acceleration sensor 24. Note that, when using the acceleration sensor 24, the arithmetic processing unit 34 stops the millimeter wave sensor 25. As a result, the power consumption of the millimeter wave sensor 25 may be reduced. With reference to the switching table 40, the arithmetic processing unit 34 also determines that the walking state of the subject is in the excessive condition if the absolute value of the amount of change (differential value) in heart rate is 6 bpm or more, and starts the millimeter wave sensor 25. Note that, even when starting the millimeter wave sensor 25, the arithmetic processing unit 34 uses the acceleration sensor 24 without stopping the acceleration sensor 24.

If the walking state of the subject is in the excessive condition, the arithmetic processing unit 34 starts the millimeter wave sensor 25 so as to calculate the heart rate, and thereby calculates an accurate exercise intensity. If the walking state of the subject is in the stationary condition, the arithmetic processing unit 34 stops the millimeter wave sensor 25 and uses the acceleration sensor 24 so as to calculate an exercise intensity based on the acceleration.

Figure 5:
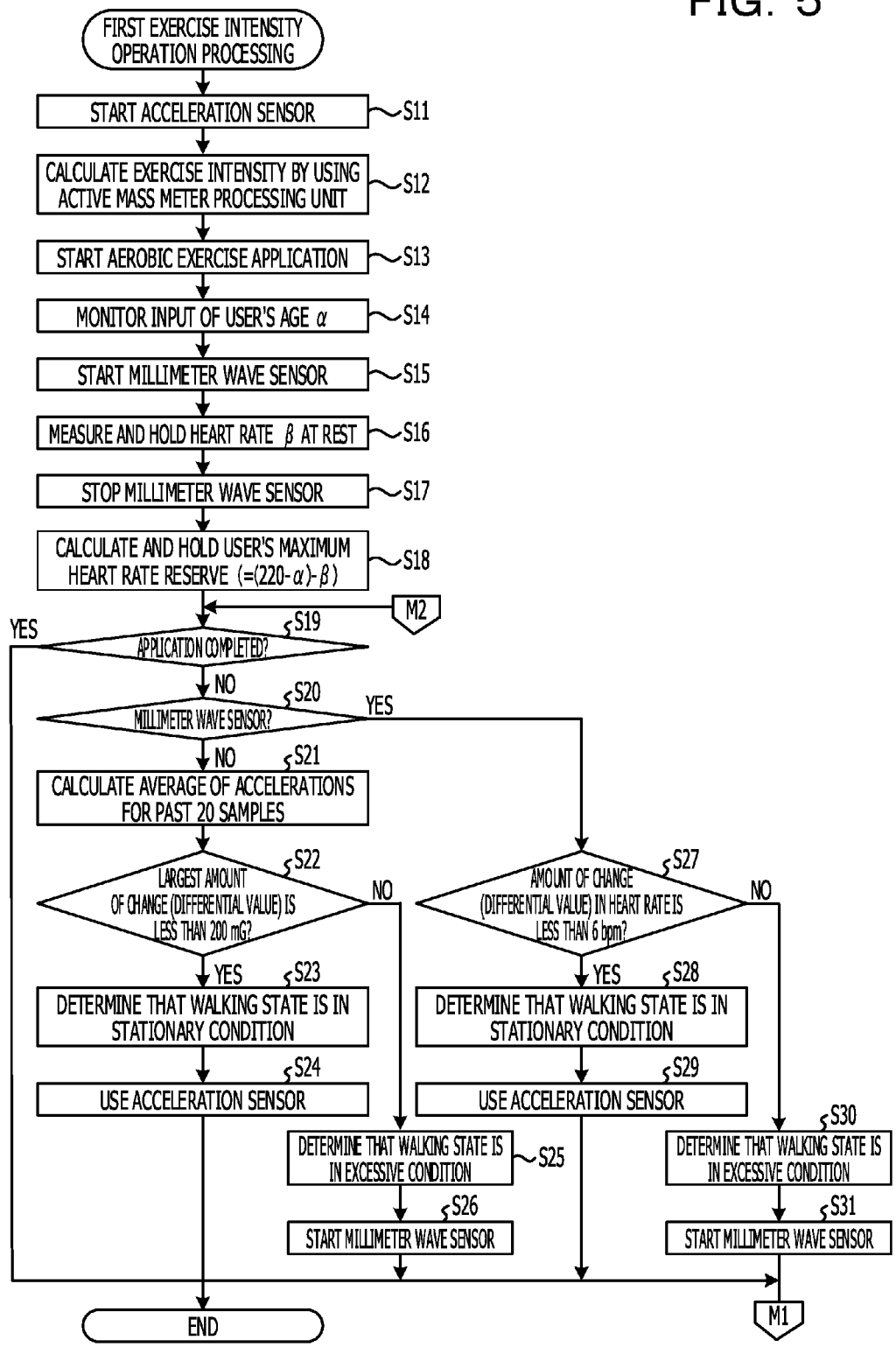
FIG. 5 is a flowchart illustrating an example of processing operations of a subprocessor of a portable terminal concerned with first exercise intensity operation processing.

Operations of the portable terminal 1 of the first embodiment will be described next. FIG. 5 is a flowchart illustrating an example of processing operations of the subprocessor 22 of the portable terminal 1 concerned with first exercise intensity operation processing of the first embodiment. The first exercise intensity operation processing illustrated in FIG. 5 is processing for notifying the application 28A of an exercise intensity suitable for the current walking state of the subject.

Figure 4A:
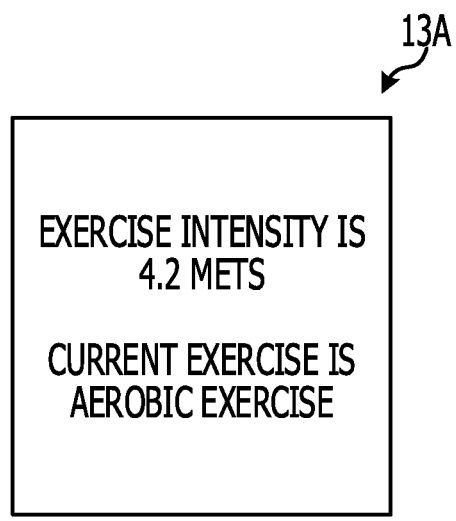
FIG. 4A is an explanatory illustration of an example of a display screen (exercise intensity information) of a portable terminal.
Figure 4B:
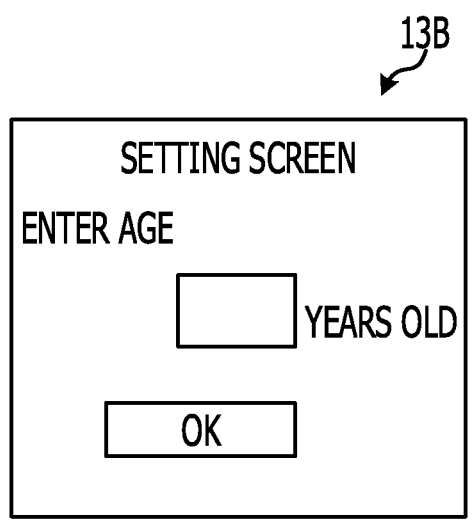
FIG. 4B is an explanatory illustration of an example of a display screen (age input screen) of the portable terminal.

In FIG. 5, the arithmetic processing unit 34 of the subprocessor 22 starts the acceleration sensor 24 (step S11). The arithmetic processing unit 34 calculates an exercise intensity by using the activity calculation processing unit 32 (step S12). The arithmetic processing unit 34 starts an aerobic exercise application (step S13), and monitors the input of a user's age a to an age input field on a setting screen 13B illustrated in FIG. 4B (step S14).

The arithmetic processing unit 34 receives the input of the age $\alpha$ and then starts the millimeter wave sensor 25 (step S15). Note that starting of the millimeter wave sensor 25 is starting of supply of electricity to the millimeter wave sensor 25. The arithmetic processing unit 34 measures a heart rate 13 of the user at rest through the millimeter wave sensor 25, and holds the heart rate $\beta$ in a storage area (not illustrated) in the RAM 26 (step S16). The arithmetic processing unit 34 stops the millimeter wave sensor 25 (step S17). Note that stopping of the millimeter wave sensor 25 is stopping of supply of electricity to the millimeter wave sensor 25. The arithmetic processing unit 34 calculates the user's maximum heart rate reserve $\gamma$, and holds the maximum heart rate reserve $\gamma$ in the storage area in the RAM 26 (step S18). Note that the maximum heart rate reserve $\gamma$ is an index used at the time of calculating an exercise intensity. The arithmetic processing unit 34 calculates the maximum heart rate reserve $\gamma$ using $(220-\alpha)-\beta$.

The arithmetic processing unit 34 determines whether the current application 28A has been completed (step S19). If the current application 28A has been completed (affirmative in step S19), the arithmetic processing unit 34 terminates the processing operations of FIG. 5. If the current application 28A has not been completed (negative in step S19), the arithmetic processing unit 34 determines whether a sensor currently in use is the millimeter wave sensor 25 (step S20). If the sensor currently in use is not the millimeter wave sensor 25 (negative in step S20), the arithmetic processing unit 34 uses the acceleration sensor 24 and calculates the average of accelerations for the past 20 samples (step S21).

The arithmetic processing unit 34 determines whether the largest amount of change (differential value) in the average of accelerations between the current samples and the previous or subsequent samples is less than a threshold, for example, 200 mG (step S22). If the largest amount of change (differential value) is less than 200 mG (affirmative in step S22), the amount of change is small, and therefore the arithmetic processing unit 34 determines that the walking state of the subject is in the stationary condition (step S23). Then, the arithmetic processing unit 34 refers to the switching table 40 of FIG. 3 and uses the acceleration sensor 24 (step S24), and proceeds to M1 illustrated in FIG. 6. Note that the arithmetic processing unit 34 stops the millimeter wave sensor 25 if the walking state of the subject is in the stationary condition.

Otherwise, if the largest amount of change (differential value) is not less than 200 mG (negative in step S22), the amount of change is large, and therefore the arithmetic processing unit 34 determines that the walking state of the subject is in the excessive condition (step S25). Then, the arithmetic processing unit 34 refers to the switching table 40 and starts the millimeter wave sensor 25 (step S26), and proceeds to M1 illustrated in FIG. 6.

If the sensor currently in use is the millimeter wave sensor 25 (affirmative in step S20), the arithmetic processing unit 34 determines whether the amount of change (differential value) in heart rate is less than a heart rate threshold, for example, 6 bpm (step S27). If the amount of change (differential value) in heart rate is less than 6 bpm (affirmative in step S27), the amount of change is small, and therefore the arithmetic processing unit 34 determines that the walking state of the subject is in the stationary condition (step S28). Then, the arithmetic processing unit 34 refers to the switching table 40 and uses the acceleration sensor 24 (step S29), and proceeds to M1 illustrated in FIG. 6. Note that the arithmetic processing unit 34 stops the millimeter wave sensor 25 if the walking state of the subject is in the stationary condition.

If the amount of change (differential value) in heart rate is not less than 6 bpm (negative in step S27), the amount of change is large, and therefore the arithmetic processing unit 34 determines that the walking state of the subject is in the excessive condition (step S30). Then, the arithmetic processing unit 34 refers to the switching table 40 and starts the millimeter wave sensor 25 (step S31), and proceeds to M1 of FIG. 6.

Figure 6:
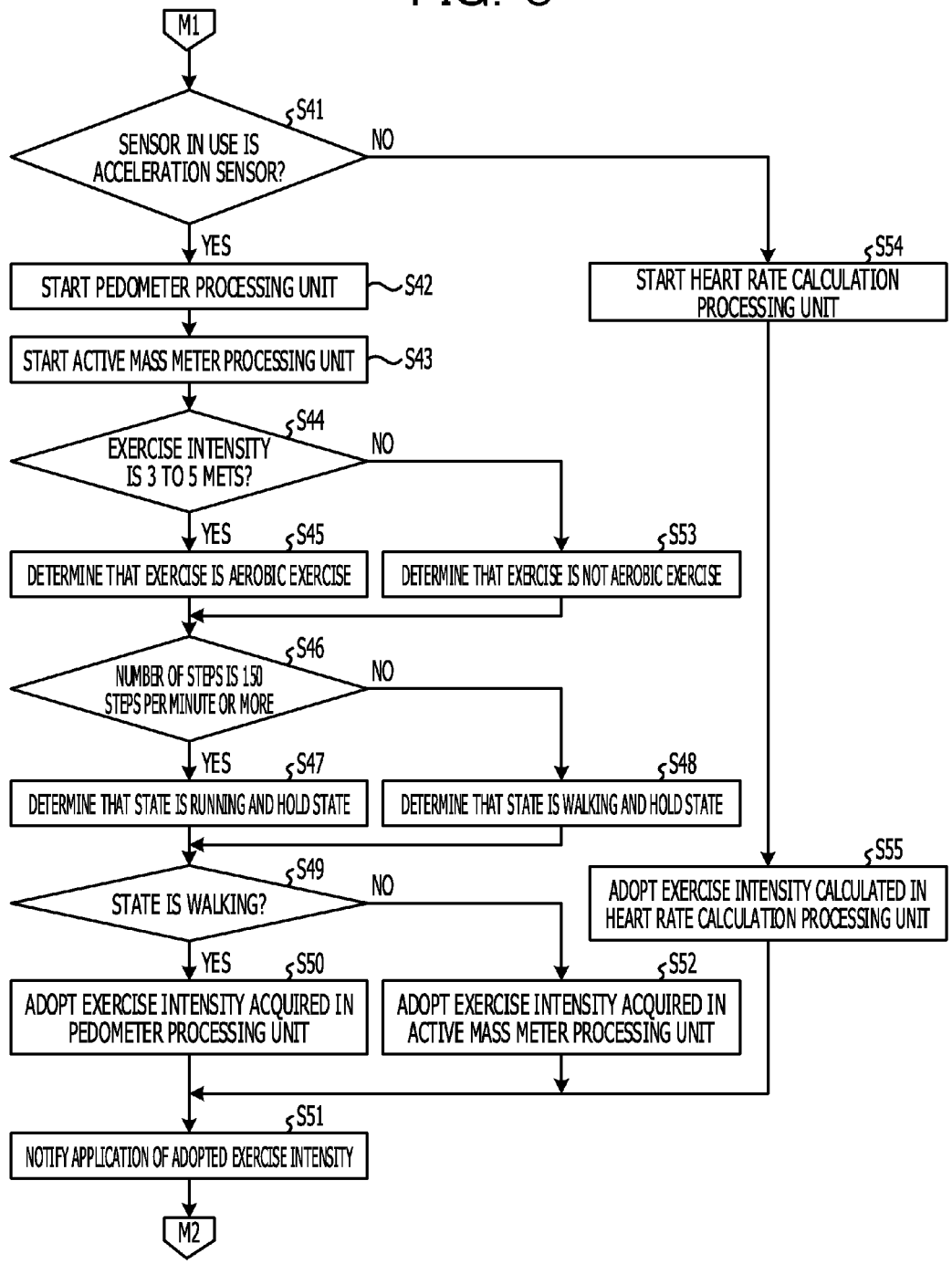
FIG. 6 is a flowchart illustrating an example of processing operations of the subprocessor of the portable terminal concerned with the first exercise intensity operation processing.

In M1 of FIG. 6, the arithmetic processing unit 34 determines whether a sensor in use is the acceleration sensor 24 (step S41). If the sensor in use is the acceleration sensor 24 (affirmative in step S41), the arithmetic processing unit 34 starts the pedometer processing unit 31 (step S42). Additionally, the arithmetic processing unit 34 starts the activity calculation processing unit 32 (step S43). Then, the arithmetic processing unit 34 determines whether the exercise intensity acquired by using the pedometer processing unit 31 and the activity calculation processing unit 32 is within the range from 3 to 5 METs (step S44). Note that an exercise level EX may be used instead of the exercise intensity METs as an index. If the exercise intensity is within the range from 3 to 5 METs (affirmative in step S44), the arithmetic processing unit 34 determines that the exercise is aerobic exercise (step S45).

Additionally, the arithmetic processing unit 34 determines whether the number of steps obtained in the pedometer processing unit 31 is 150 steps per minute or more (step S46). If the number of steps is 150 steps per minute or more (affirmative in step S46), the arithmetic processing unit 34 determines that the state of exercise is "running", and holds the state of exercise as being the running state in the storage area in the RAM 26 (step S47). If the number of steps is not 150 steps per minute or more (negative in step S46), the arithmetic processing unit 34 determines that the state of exercise is "walking", and holds the state of exercise as being the walking state in the storage area in the RAM 26 (step S48).

Additionally, on the basis of the state of exercise being held in the storage area, the arithmetic processing unit 34 determines whether the state of exercise is the walking state (step S49). If the state of exercise is the walking state (affirmative in step S49), the arithmetic processing unit 34 adopts an exercise intensity acquired in the pedometer processing unit 31 (step S50), and notifies the application 28A in the application CPU 28 of the adopted exercise intensity (step S51), and proceeds to M2 illustrated in FIG. 5. As a result, the application 28A determines on the basis of the exercise intensity whether the exercise is aerobic exercise. The application 28A also determines whether the subject has woken up from sleep, for example. The application 28A determines on the basis of the exercise intensity whether the exercise is aerobic exercise, and displays a report content 13A of FIG. 4A on the LCD 13 if the exercise is aerobic exercise. Seeing the report content 13A enables the user to recognize that the exercise intensity is 4.2 METs and the aerobic exercise is currently being carried out.

Otherwise, if the state of exercise is not the walking state (negative in step S49), the arithmetic processing unit 34 determines that the state of exercise is running, and adopts the exercise intensity acquired in the activity calculation processing unit 32 (step S52), and proceeds to step S51 in order to notify the application 28A of the adopted exercise intensity.

If the exercise intensity is not within the range from 3 to 5 METs (negative in step S44), the arithmetic processing unit 34 determines that the exercise is not aerobic exercise (step S53), and proceeds to step S46 in order to determine whether the number of steps is 150 steps per minute or more.

If the sensor in use is not the acceleration sensor 24 (negative in step S41), the arithmetic processing unit 34 determines that the millimeter wave sensor 25 is in use, and starts the heart rate calculation processing unit 33 (step S54). After the start of the heart rate calculation processing unit 33, the arithmetic processing unit 34 adopts an exercise intensity calculated in the heart rate calculation processing unit 33 (step S55), and proceeds to step S51 in order to notify the application 28A of the adopted exercise intensity. The application 28A may acquire an accurate exercise intensity obtained by the heart rate calculation processing unit 33.

If the largest amount of change (differential value) of the average of accelerations is less than 200 mG, the amount of change in the walking state is small, and therefore the arithmetic processing unit 34 of the first exercise intensity operation processing determines that the walking state of the subject is in the stationary condition, and acquires an exercise intensity obtained by using the acceleration sensor 24. As a result, the arithmetic processing unit 34 stops the millimeter wave sensor 25 and acquires an exercise intensity by using the acceleration sensor 24, and it is possible to reduce the power consumption of the entirety of the portable terminal 1 by an amount of power corresponding to the stopped millimeter wave sensor 25.

If the largest amount of change (differential value) of the average of accelerations is not less than 200 mG, the amount of change in the walking state is large, and therefore the arithmetic processing unit 34 determines that the walking state of the subject is in the excessive condition, and acquires an exercise intensity obtained by using the millimeter wave sensor 25. As a result, the arithmetic processing unit 34 may acquire an accurate exercise intensity by using the millimeter wave sensor 25 if the walking state is in the excessive condition.

If the amount of change in heart rate is less than 6 bpm, the amount of change is small, and therefore the arithmetic processing unit 34 determines that the walking state of the subject is in the stationary condition, and acquires an exercise intensity obtained by using the acceleration sensor 24. As a result, the arithmetic processing unit 34 stops the millimeter wave sensor 25 and acquires an exercise intensity by using the acceleration sensor 24, and it is possible to reduce the power consumption of the entirety of the portable terminal 1 by an amount of power corresponding to the stopped millimeter wave sensor 25.

If the amount of change in heart rate is not less than 6 bpm, the amount of change is large, and therefore the arithmetic processing unit 34 determines that the walking state of the subject is in the excessive condition, and acquires an exercise intensity obtained by using the millimeter wave sensor 25. As a result, the arithmetic processing unit 34 may acquire an accurate exercise intensity by using the millimeter wave sensor 25 if the walking state is in the excessive condition.

If the subject is in a walking state, the arithmetic processing unit 34 adopts an exercise intensity obtained in the pedometer processing unit 31. As a result, the arithmetic processing unit 34 may acquire an exercise intensity in accordance with the walking speed.

If the subject is not in the walking state, the arithmetic processing unit 34 adopts an exercise intensity obtained in the activity calculation processing unit 32. As a result, the arithmetic processing unit 34 may acquire an exercise intensity based on the accelerations averaged for one second.

If the sensor in use is not the acceleration sensor 24, that is, if the sensor in use is the millimeter wave sensor 25, the arithmetic processing unit 34 adopts an exercise intensity obtained by using the heart rate calculation processing unit 33. As a result, the arithmetic processing unit 34 may acquire an exercise intensity in accordance with the proportion of the current heart rate with respect to the maximum heart rate reserve.

Figure 7:
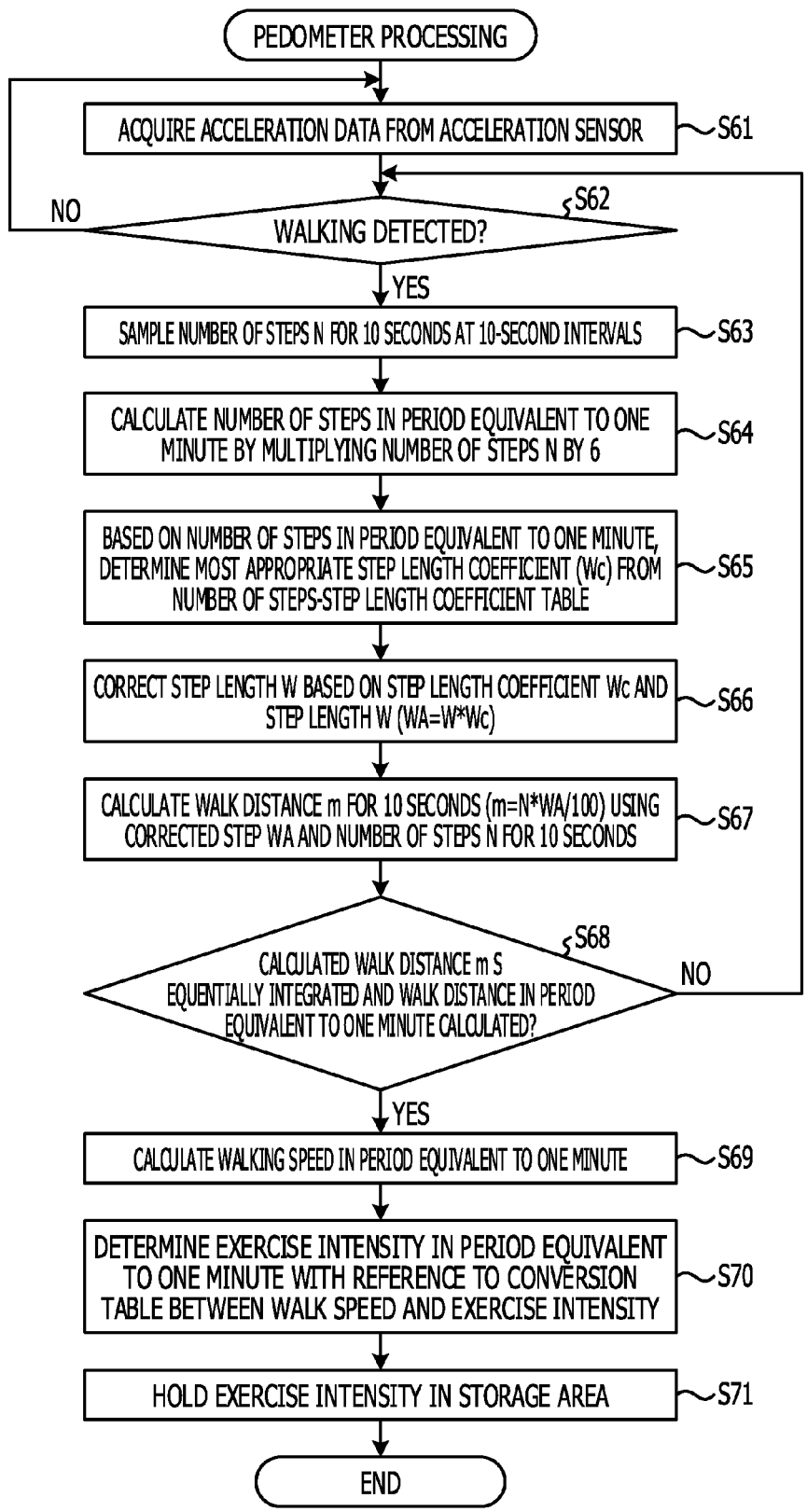
FIG. 7 is a flowchart illustrating an example of processing operations of the subprocessor of the portable terminal concerned with pedometer processing.

FIG. 7 is a flowchart illustrating an example of processing operations of the subprocessor 22 of the portable terminal 1 concerned with pedometer processing. The pedometer processing illustrated in FIG. 7 is processing that calculates a walking speed in a period equivalent to one minute based on the accelerations detected in the acceleration sensor 24 and acquires an exercise intensity based on the calculated walking speed.

In FIG. 7, the pedometer processing unit 31 acquires acceleration data from the acceleration sensor 24 (step S61) and determines whether walking has been detected (step S62). If walking has been detected (affirmative in step S62), the pedometer processing unit 31 samples the number of steps N for 10 seconds at 10-second intervals (step S63) and calculates the number of steps in a period equivalent to one minute by multiplying the number of steps N by six (step S64). On the basis of the number of steps in a period equivalent to one minute, the pedometer processing unit 31 determines a step length coefficient Wc corresponding to the number of steps with reference to a table (not illustrated) between the number of steps and the step length coefficient in the ROM 27 (step S65).

The pedometer processing unit 31 calculates a corrected step length WA using "WA=Wc*W", where Wc is the determined step length coefficient and W is a step length (step S66). Note that the step length W is input in response to the user's setting operations. The pedometer processing unit 31 calculates a walk distance m for 10 seconds using "m=N*WA/100", where WA is the corrected step and N is the number of steps for 10 seconds (step S67). Additionally, the pedometer processing unit 31 determines whether the calculated walk distance m has been sequentially integrated, and the walk distance over which the subject reaches in a period equivalent to one minute has been calculated (step S68).

If the walk distance over which the subject reaches in a period equivalent to one minute has been calculated (affirmative in step S68), the pedometer processing unit 31 calculates a walking speed in a period equivalent to one minute on the basis of the walk distance in a period equivalent to one minute (step S69). Additionally, the pedometer processing unit 31 determines an exercise intensity in a period equivalent to one minute with reference to the conversion table between the walk speed and the exercise intensity in the ROM 27 (step S70). After the determination of the exercise intensity in a period equivalent to one minute, the pedometer processing unit 31 holds the exercise intensity in the storage area in the RAM 26 (step S71), and ends the processing operations of FIG. 7.

If the walk distance over which the subject reaches in a period equivalent to one minute has not been calculated (negative in step S68), the pedometer processing unit 31 proceeds to step S62 so that processing operations are repeated in such a manner that, initially, the operations from S62 to S67 are performed six times, until the walk distance m corresponding to the number of steps for 60 seconds is calculated. If walking has not been detected (negative in step S62), the pedometer processing unit 31 proceeds to step S61.

The pedometer processing unit 31 calculates the number of steps for one minute using the number of steps based on the acceleration of the acceleration sensor 24, determines the step length coefficient corresponding to the number of steps, corrects the step length input by the user on the basis of the step length coefficient, and calculates the walk distance for 10 seconds on the basis of the corrected step length and the number of steps for 10 seconds. Additionally, the pedometer processing unit 31 sequentially integrates the walk distance for 10 seconds to acquire the walk distance in a period equivalent to one minute, calculates a walk speed on the basis of the walk distance in a period equivalent to one minute, and acquires an exercise intensity in a period equivalent to one minute corresponding to the walk speed. As a result, the arithmetic processing unit 34 may acquire the exercise intensity in a period equivalent to one minute by using the pedometer processing unit 31.

Figure 8:
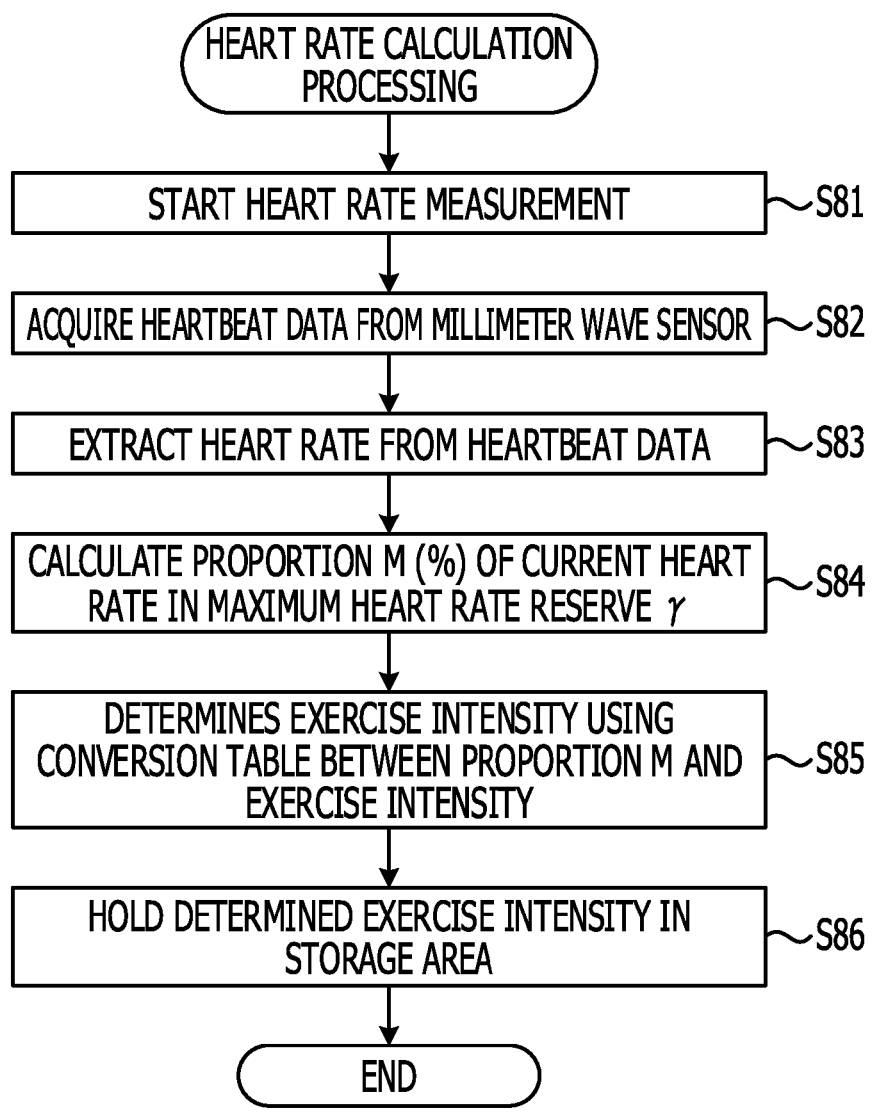
FIG. 8 is a flowchart illustrating an example of processing operations of the subprocessor of the portable terminal concerned with heart rate calculation processing.

FIG. 8 is a flowchart illustrating an example of processing operations of the subprocessor 22 of the portable terminal 1 concerned with heart rate calculation processing. The heart rate calculation processing illustrated in FIG. 8 is processing that acquires an exercise intensity based on the proportion of the current heart rate with respect to the maximum heart rate reserve.

In FIG. 8, the heart rate calculation processing unit 33 starts a measurement operation of a heart rate by using the millimeter wave sensor 25 (step S81), and acquires heartbeat data from the millimeter wave sensor 25 (step S82). Note that noise data due to the motion and the like of the subject other than heartbeats is mixed in the heartbeat data.

The heart rate calculation processing unit 33 removes noise from the heartbeat data to extract only heartbeats, thereby obtaining an accurate heart rate (step S83). The heart rate calculation processing unit 33 calculates the proportion M (%) of the current heart rate in the maximum heart rate reserve γ (step S84).

With reference to the conversion table of the exercise intensity corresponding to the proportion M (%) of the current heart rate in the maximum heart rate reserve γ, the heart rate calculation processing unit 33 determines an exercise intensity corresponding to the proportion M (%) of the current heart rate in the maximum heart rate reserve γ (step S85). Then, the heart rate calculation processing unit 33 holds the determined exercise intensity in the storage area in the RAM 26 (step S86), and ends the processing operations of FIG. 8.

The heart rate calculation processing unit 33 in the heart rate calculation processing illustrated in FIG. 8 acquires the exercise intensity corresponding to the proportion M (%) of the current heart rate in the maximum heart rate reserve γ. As a result, the arithmetic processing unit 34 may acquire an accurate exercise intensity corresponding to the current heart rate.

Figure 9:
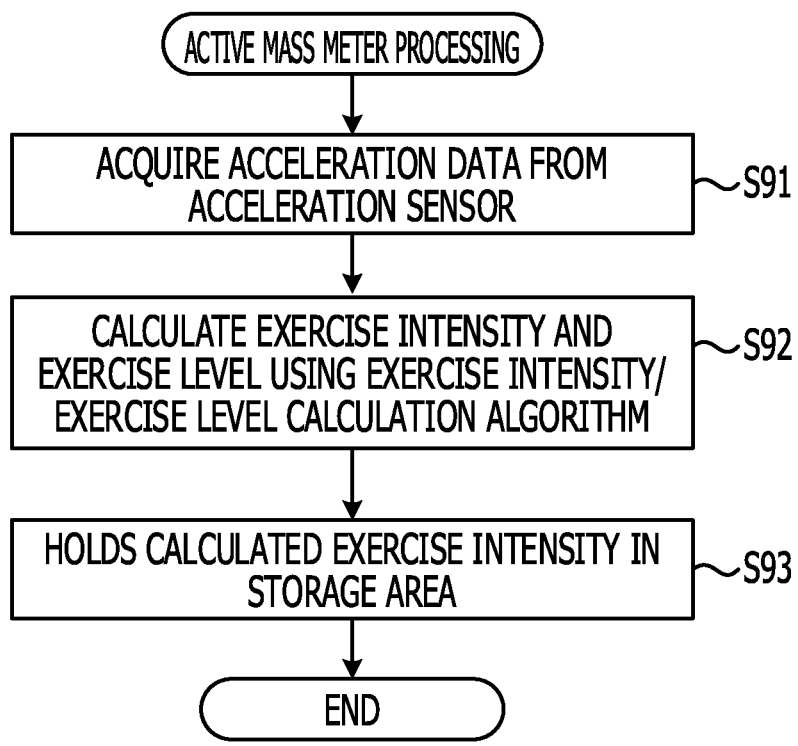
FIG. 9 is a flowchart illustrating an example of processing operations of the subprocessor of the portable terminal concerned with activity calculation processing.

FIG. 9 is a flowchart illustrating an example of processing operations of the subprocessor 22 of the portable terminal 1 concerned with activity calculation processing. The activity calculation processing illustrated in FIG. 9 is processing that calculates an exercise intensity based on the acceleration detected in the acceleration sensor 24 using an exercise intensity/exercise level calculation algorithm.

In FIG. 9, the activity calculation processing unit 32 acquires acceleration data from the acceleration sensor 24 (step S91), and calculates an exercise intensity and an exercise level using the exercise intensity/exercise level calculation algorithm (step S92). The activity calculation processing unit 32 holds the calculated exercise intensity in the storage area (not illustrated) in the RAM 26 (step S93), and ends the processing operations of FIG. 9.

Using the exercise intensity/exercise level calculation algorithm, the activity calculation processing unit 32 of the activity calculation processing illustrated in FIG. 9 calculates an exercise intensity based on the acceleration detected by the acceleration sensor 24. As a result, the arithmetic processing unit 34 may acquire an exercise intensity based on the acceleration.

If the largest amount of change (differential value) of the average of accelerations is less than 200 mG, the amount of change in the walking state is small, and therefore the arithmetic processing unit 34 of the first embodiment determines that the walking state of the subject is in the stationary condition, and acquires an exercise intensity obtained by using the acceleration sensor 24. As a result, the arithmetic processing unit 34 stops the millimeter wave sensor 25 and acquires an exercise intensity by using the acceleration sensor 24, and it is possible to reduce the power consumption of the entirety of the portable terminal 1 by an amount of power corresponding to the stopped millimeter wave sensor 25.

If the largest amount of change (differential value) of the average of accelerations is not less than 200 mG, the amount of change in the walking state is large, and therefore the arithmetic processing unit 34 determines that the walking state of the subject is in the excessive condition, and acquires an exercise intensity obtained by using the millimeter wave sensor 25. As a result, the arithmetic processing unit 34 may acquire an accurate exercise intensity by using the millimeter wave sensor 25 if the walking state of the subject is in the excessive condition.

If the amount of change in heart rate is less than 6 bpm, the amount of change is small, and therefore the arithmetic processing unit 34 determines that the walking state of the subject is in the stationary condition, and acquires an exercise intensity obtained by using the acceleration sensor 24. As a result, the arithmetic processing unit 34 stops the millimeter wave sensor 25 and acquires an exercise intensity by using the acceleration sensor 24, and it is possible to reduce the power consumption of the entirety of the portable terminal 1 by an amount of power corresponding to the stopped millimeter wave sensor 25.

If the amount of change in heart rate is not less than 6 bpm, the amount of change is large, and therefore the arithmetic processing unit 34 determines that the walking state of the subject is in the excessive condition, and acquires an exercise intensity obtained by using the millimeter wave sensor 25. As a result, the arithmetic processing unit 34 may acquire an accurate exercise intensity by using the millimeter wave sensor 25 if the walking state of the subject is in the excessive condition.

If the subject is in a walking state, the arithmetic processing unit 34 adopts an exercise intensity obtained in the pedometer processing unit 31. As a result, the arithmetic processing unit 34 may acquire an exercise intensity in accordance with the walking speed.

If the subject is not in the walking state, the arithmetic processing unit 34 adopts an exercise intensity obtained in the activity calculation processing unit 32. As a result, the arithmetic processing unit 34 may acquire an exercise intensity based on an acceleration averaged for one second.

If the sensor in use is not the acceleration sensor 24, that is, if the sensor in use is the millimeter wave sensor 25, the arithmetic processing unit 34 adopts an exercise intensity obtained in the heart rate calculation processing unit 33. As a result, the arithmetic processing unit 34 may acquire an exercise intensity in accordance with the proportion of the current heart rate with respect to the maximum heart rate reserve.

Note that, in the above first embodiment, if the walking state of the subject is in the excessive condition, the millimeter wave sensor 25 is used without stopping the acceleration sensor 24; however, the acceleration sensor 24 may be stopped.

Figure 10:
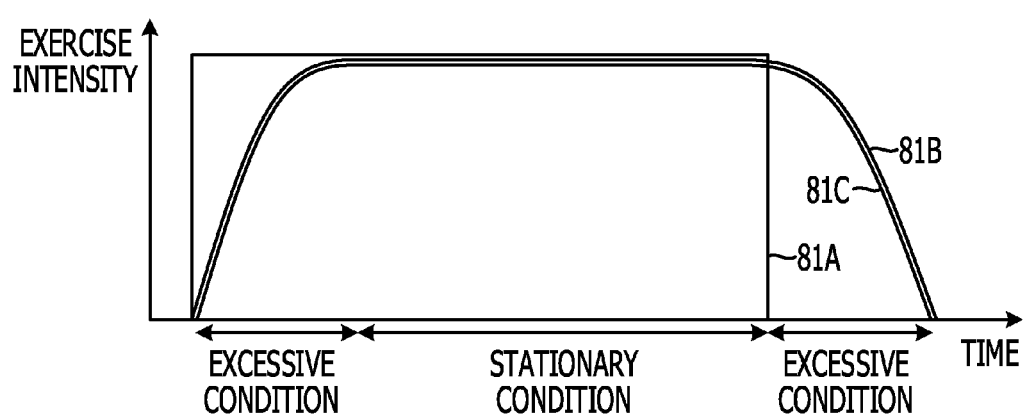
FIG. 10 is an explanatory graph illustrating the relationship among the exercise intensity calculated by using an acceleration sensor, the actual exercise intensity, and the exercise intensity calculated by using a millimeter wave sensor.

FIG. 10 is an explanatory graph illustrating the relationship among the exercise intensity calculated by using the acceleration sensor 24, the actual exercise intensity, and the exercise intensity calculated by using the millimeter wave sensor 25. The relationship among an exercise intensity 81A calculated by using the acceleration sensor, an exercise intensity 81B actually received by a person, and an exercise intensity 81C calculated by using the millimeter wave sensor 25 is as illustrated in FIG. 10. The exercise intensity 81B received by a person is smaller than the intensity of exercise actually performed by a person for several minutes from the start of exercise to a time point at which the stationary state is reached. In contrast, the exercise intensity 81B received by a person during exercise and during stopping of exercise is larger than the intensity of exercise actually performed by a person for several minutes from the stopping of exercise to a time point at which the stationary state is reached. This is because the function for relaxing a rapid load change acts on the body of a person. When an exercise intensity is calculated by using only the acceleration sensor 24 that consumes less power, only the exercise performed by a person is grasped by the sensor. This does not enable an accurate exercise intensity to be calculated when the walking state of the subject is in the excessive condition. However, as in the embodiment described above, such a mechanism that the acceleration sensor 24 is started in the stationary condition and the millimeter wave sensor 25 is started in the excessive condition is adopted. This enables an exercise intensity to be accurately calculated for exercise in any state of a person, and enables the amount of power consumption to be suppressed.

In the above first embodiment, it is determined, on the basis of the results of detection made by the acceleration sensor 24 and the millimeter wave sensor 25, whether the walking state of the subject is in the excessive condition. However, the result of detection made by a gyroscope sensor integrated in the portable terminal 1 may be used. The embodiment in this case will be described as a second embodiment below.

Second Embodiment

Figure 11:
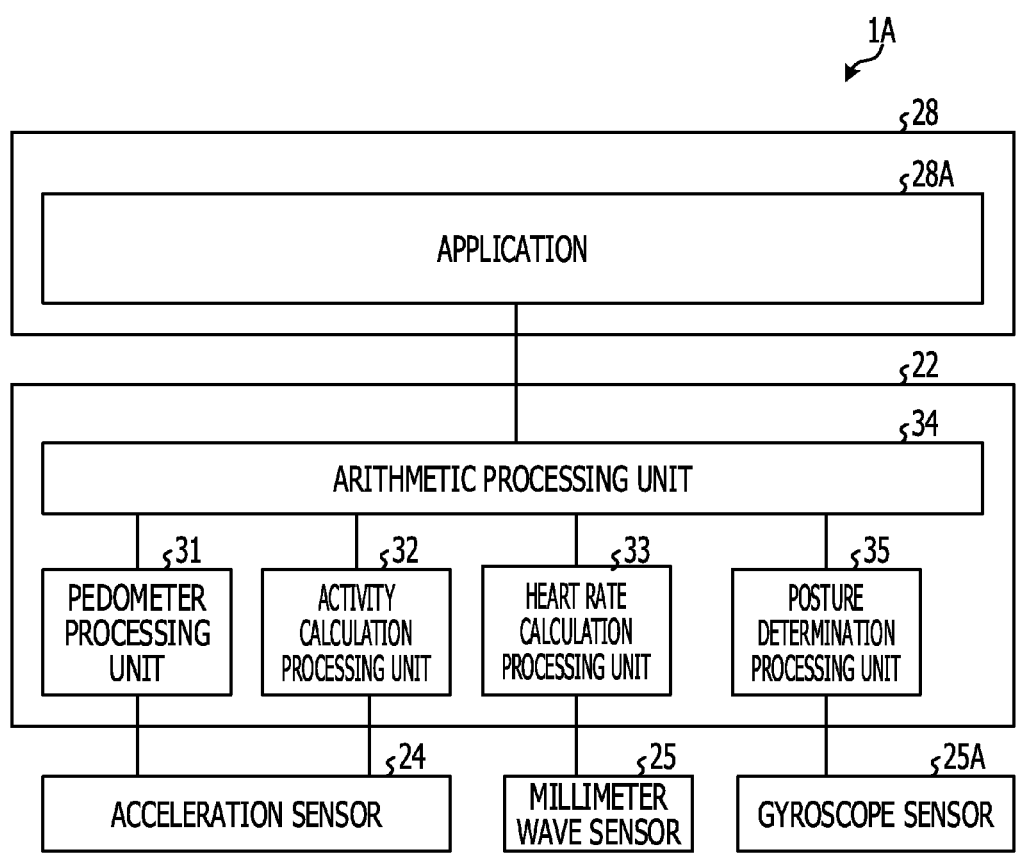
FIG. 11 is an explanatory diagram illustrating an example of a functional configuration of an application CPU and a subprocessor of a second embodiment.

FIG. 11 is an explanatory diagram illustrating an example of a functional configuration of the application CPU 28 and the subprocessor 22 of the second embodiment. Note that the same configurations as the portable terminal 1 of the first embodiment are denoted by the same reference characters, and the descriptions of the overlapping configurations and operations will be omitted. A portable terminal 1A illustrated in FIG. 11 differs from the portable terminal 1 of the first embodiment in that it is determined on the basis of a result of detection made by a gyroscope sensor 25A whether the walking state of the subject is in the excessive condition.

The subprocessor 22 illustrated in FIG. 11 includes a posture determination processing unit 35 other than the pedometer processing unit 31, the activity calculation processing unit 32, the heart rate calculation processing unit 33, and the arithmetic processing unit 34. The posture determination processing unit 35 determines on the basis of a result of detection made by the gyroscope sensor 25A whether the walking state of the subject is in the excessive condition.

Figure 12:
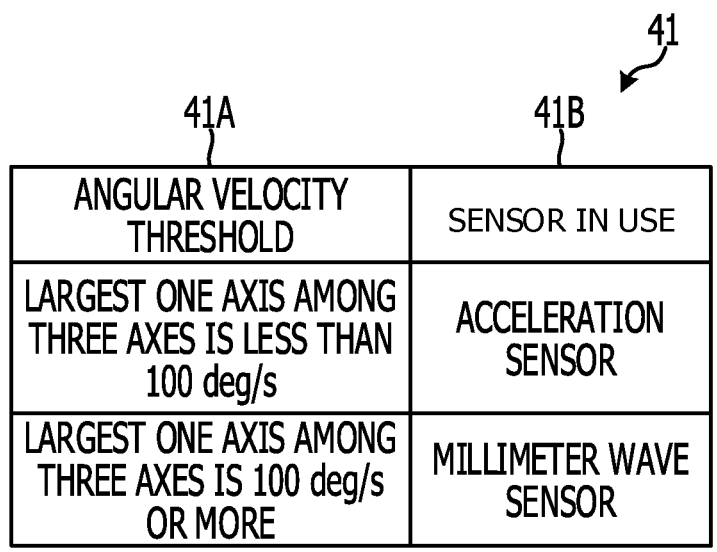
FIG. 12 is an explanatory illustration of an example of a switching table of the second embodiment.

A switching table 41 illustrated in FIG. 12 is stored in the RAM 26. FIG. 12 is an explanatory illustration of an example of the switching table 41 of the second embodiment. The switching table 41 illustrated in FIG. 12 manages an angular velocity threshold 41A and a sensor in use 41B in association with each other. The angular velocity threshold 41A is compared to the largest amount of change (differential value) that is a difference between the average of 20 samples for each of an x-axis angular velocity, a y-axis angular velocity, and a z-axis angular velocity detected by the gyroscope sensor 25A, and the average of the previous 20 samples. The angular velocity threshold 41A is a threshold for determining whether the walking state of the subject is in the excessive condition. If the largest amount of change (differential value) among the amounts of change (differential value) of the three axes is less than the angular velocity threshold 41A, for example, 100 deg/s, the amount of change in the walking state is small, and therefore the arithmetic processing unit 34 uses the acceleration sensor 24 with reference to the switching table 41. If the largest amount of change (differential value) among the amounts of change differences of the three axes is 100 deg/s or more, the amount of change in the walking state is large, and therefore the arithmetic processing unit 34 uses the millimeter wave sensor 25 with reference to the switching table 41.

Figure 13:
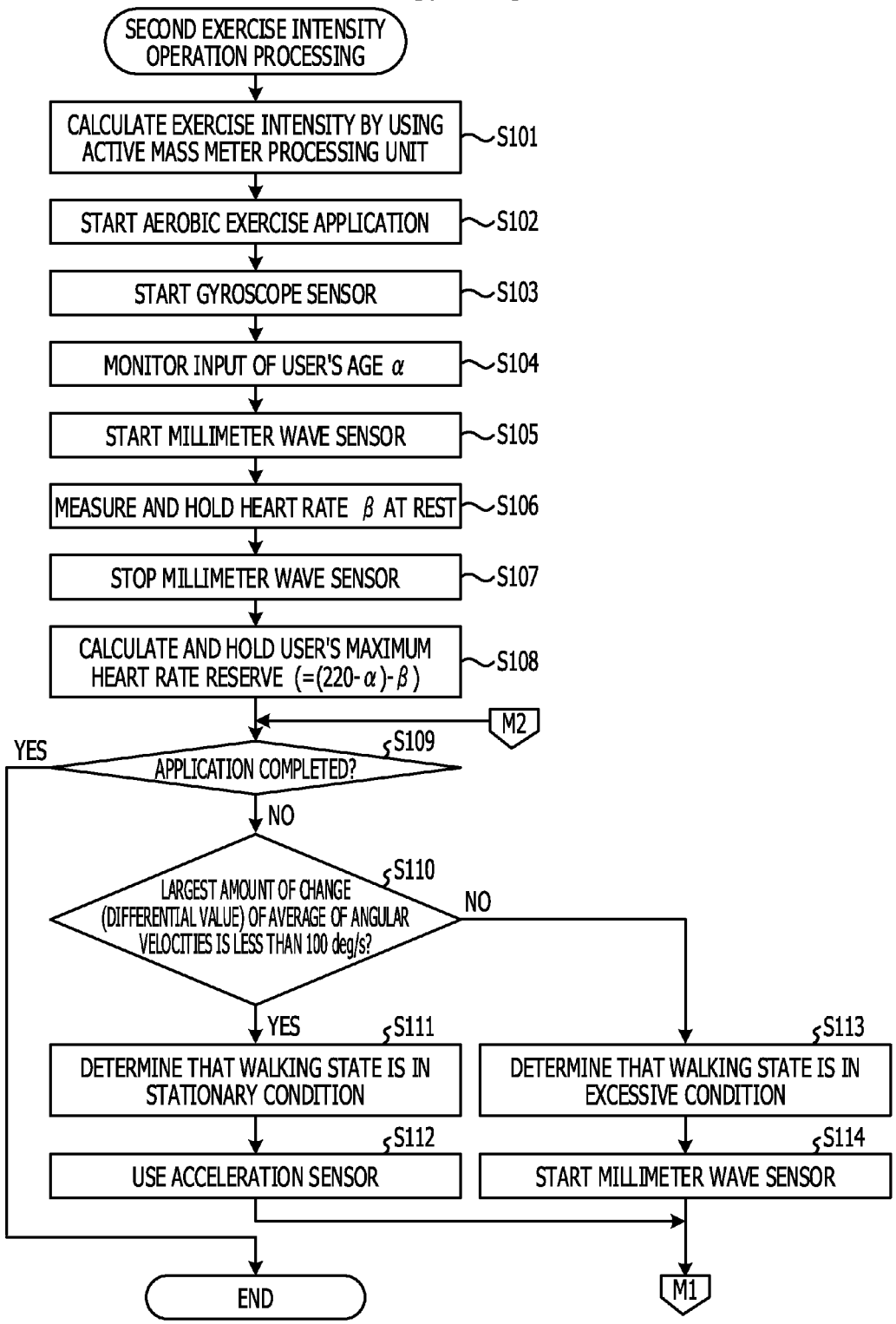
FIG. 13 is a flowchart illustrating an example of processing operations of a subprocessor of a portable terminal concerned with second exercise intensity operation processing.

Operations of the portable terminal 1A of the second embodiment will be described next. FIG. 13 is a flowchart illustrating an example of processing operations of the subprocessor 22 of the portable terminal 1A concerned with second exercise intensity operation processing of the second embodiment. The second exercise intensity operation processing illustrated in FIG. 13 is processing in which it is determined, on the basis of a result of detection made by the gyroscope sensor 25A, whether the walking state of the subject is in the excessive condition, and the application 28A is notified of an exercise intensity suitable for the current walking state.

As illustrated In FIG. 13, the arithmetic processing unit 34 calculates an exercise intensity by using the activity calculation processing unit 32 (step S101). The arithmetic processing unit 34 starts an aerobic exercise application (step S102), and starts the gyroscope sensor 25A (step S103). After the start of the gyroscope sensor 25A, the arithmetic processing unit 34 monitors the input of the user's age α to the age input field on the setting screen 13B illustrated in FIG. 4B (step S104).

After the input of the age α, the arithmetic processing unit 34 starts the millimeter wave sensor 25 (step S105), measures the heart rate 13 of the user at rest through the millimeter wave sensor 25, and holds the heart rate 13 in a storage area (not illustrated) in the RAM 26 (step S106). The arithmetic processing unit 34 stops the millimeter wave sensor 25 (step S107), calculates the user's maximum heart rate reserve γ, and holds the maximum heart rate reserve γ in the storage area in the RAM 26 (step S108).

The arithmetic processing unit 34 determines whether the current application 28A has been completed (step S109). The arithmetic processing unit 34 terminates the processing operations of FIG. 13 if the current application 28A has been completed (affirmative in S109). Otherwise, if the current application 28A has not been completed (negative in S109), the arithmetic processing unit 34 determines whether the largest amount of change (differential value) of the average of angular velocities of the gyroscope sensor 25A is less than an angular velocity threshold, for example, 100 deg/s (step S110).

If the largest amount of change (differential value) of the average of angular velocities of the gyroscope sensor 25A is less than 10 deg/s (affirmative in step S110), the amount of change in the walking state is small, and therefore the arithmetic processing unit 34 determines that the walking state of the subject is in the stationary condition (step S111). Then, the arithmetic processing unit 34 uses the acceleration sensor 24 (step S112), and proceeds to M1 of FIG. 6. Otherwise, if the largest amount of change (differential value) of the average of angular velocities is not less than 100 deg/s (negative in step S110), the amount of change in the walking state is large, and therefore the arithmetic processing unit 34 determines that the walking state of the subject is in the excessive condition (step S113). Then, the arithmetic processing unit 34 starts the millimeter wave sensor 25 (step S114), and proceeds to M1 of FIG. 6.

If the largest amount of change (differential value) of the average of angular velocities is less than 100 deg/s, the amount of change in the walking state is small, and therefore the arithmetic processing unit 34 of the second exercise intensity operation processing determines that the walking state of the subject is in the stationary condition, and acquires an exercise intensity obtained by using the acceleration sensor 24. As a result, the arithmetic processing unit 34 stops the millimeter wave sensor 25 and acquires an exercise intensity by using the acceleration sensor 24, and it is possible to reduce the power consumption of the entirety of the portable terminal 1A by an amount of power corresponding to the stopped millimeter wave sensor 25.

If the largest amount of change (differential value) of the average of angular velocities is not less than 100 deg/s, the amount of change in the walking state is large, and therefore the arithmetic processing unit 34 determines that the walking state of the subject is in the excessive condition, and acquires an exercise intensity obtained by using the millimeter wave sensor 25. As a result, the arithmetic processing unit 34 may acquire an accurate exercise intensity by using the millimeter wave sensor 25 if the walking state is in the excessive condition.

In the above first embodiment, it is determined, on the basis of the largest amount of change (differential value) of the average of accelerations or the amount of change (differential value) in heart rate, whether the walking state of the subject is in the excessive condition. However, the excessive condition may be determined on the basis of the number of steps and the amount of difference in exercise intensity. Then, the embodiment in this case will be described as a third embodiment below.

Third Embodiment

Figure 14:
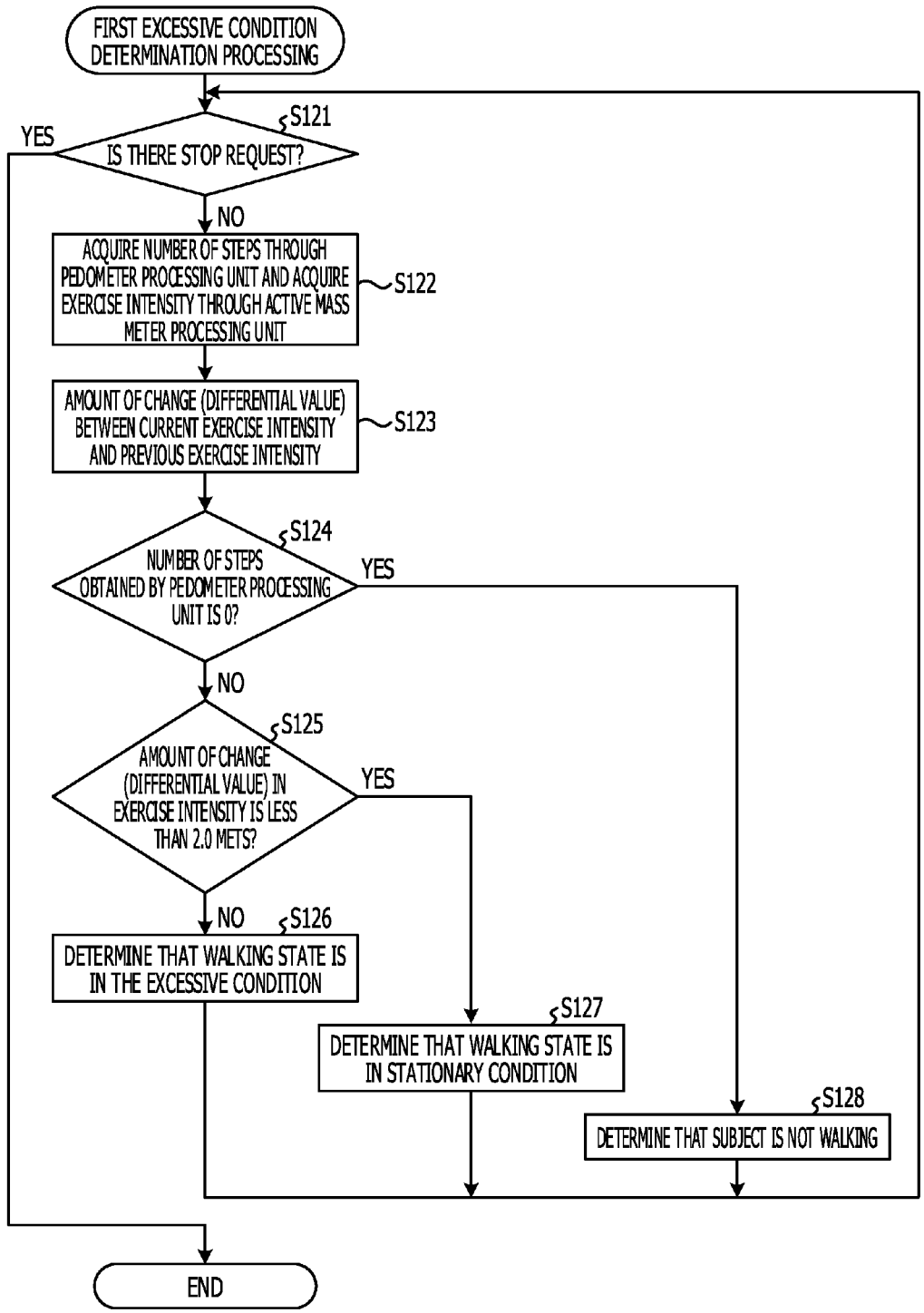
FIG. 14 is a flowchart illustrating an example of processing operations of a subprocessor of a portable terminal concerned with first excessive condition determination processing of a third embodiment.

The same configurations as the portable terminal 1 of the first embodiment are denoted by the same reference characters, and the descriptions of the overlapping configurations and operations will be omitted. FIG. 14 is a flowchart illustrating an example of processing operations of the subprocessor 22 of the portable terminal 1 concerned with first excessive condition determination processing. The first excessive condition determination processing illustrated in FIG. 14 is processing in which it is determined, on the basis of the number of steps and the amount of difference in exercise intensity, whether the walking state of the subject is in the excessive condition.

The arithmetic processing unit 34 illustrated in FIG. 14 determines whether a stop request of the application 28A has been detected (step S121). If a stop request of the application 28A has been detected (affirmative in step S121), the arithmetic processing unit 34 terminates the processing operations of FIG. 14. If a stop request of the application 28A has not been detected (negative in step S121), the arithmetic processing unit 34 acquires the number of steps through the pedometer processing unit 31 and acquires an exercise intensity through the activity calculation processing unit 32 (step S122).

The arithmetic processing unit 34 calculates the amount of change (differential value) between the current exercise intensity and the previous exercise intensity obtained one second before the present time (step S123), and determines whether the number of steps obtained by the pedometer processing unit 31 is zero (step S124). If the number of steps is not zero (negative in step S124), the arithmetic processing unit 34 determines whether the amount of change (differential value) in exercise intensity is less than 2.0 METs (step S125).

If the amount of change (differential value) in exercise intensity is not less than 2.0 METs (negative in step S125), the amount of change in the walking state is large, and therefore the arithmetic processing unit 34 determines that the walking state of the subject is in the excessive condition (step S126). Then, the arithmetic processing unit 34 proceeds to step S121 in order to determine whether there is a stop request. Otherwise, if the amount of change (differential value) in exercise intensity is less than 2.0 METs (affirmative in step S125), the amount of change in the walking state is small, and therefore the arithmetic processing unit 34 determines that the walking state of the subject is in the stationary condition (step S127), and proceeds to step S121.

If the number of steps is zero (affirmative in step S124), the arithmetic processing unit 34 determines that the subject is not walking (step S128), and proceeds to step S121.

If the number of steps is not zero and the amount of change (differential value) in exercise intensity is less than 2.0 METs, the amount of change in the walking state is small, and therefore the arithmetic processing unit 34 of the third embodiment determines that the walking state of the subject is in the stationary condition. As a result, when the walking state is in the stationary condition, the arithmetic processing unit 34 stops the millimeter wave sensor 25 and uses the acceleration sensor 24. Then, the arithmetic processing unit 34 acquires an exercise intensity by using the acceleration sensor 24, and it is possible to reduce the power consumption of the entirety of the portable terminal by an amount of power corresponding to the stopped millimeter wave sensor 25.

If the number of steps is not zero and the amount of change (differential value) between the current exercise intensity and the previous or subsequent exercise intensity is not less than 2.0 METs, the arithmetic processing unit 34 determines that the walking state of the subject is in the excessive condition. As a result, the arithmetic processing unit 34 may acquire an accurate exercise intensity by using the millimeter wave sensor 25 if the walking state is in the excessive condition.

Note that, in the above first embodiment, as described above, it is determined, on the basis of the largest amount of change (differential value) of the average of accelerations or the amount of change (differential value) in heart rate, whether the walking state of the subject is in the excessive condition; however, the excessive condition may be determined on the basis of the elapsed time from the occurrence of a change in heart rate. Then, the embodiment in this case will be described as a fourth embodiment below.

Fourth Embodiment

Figure 15:
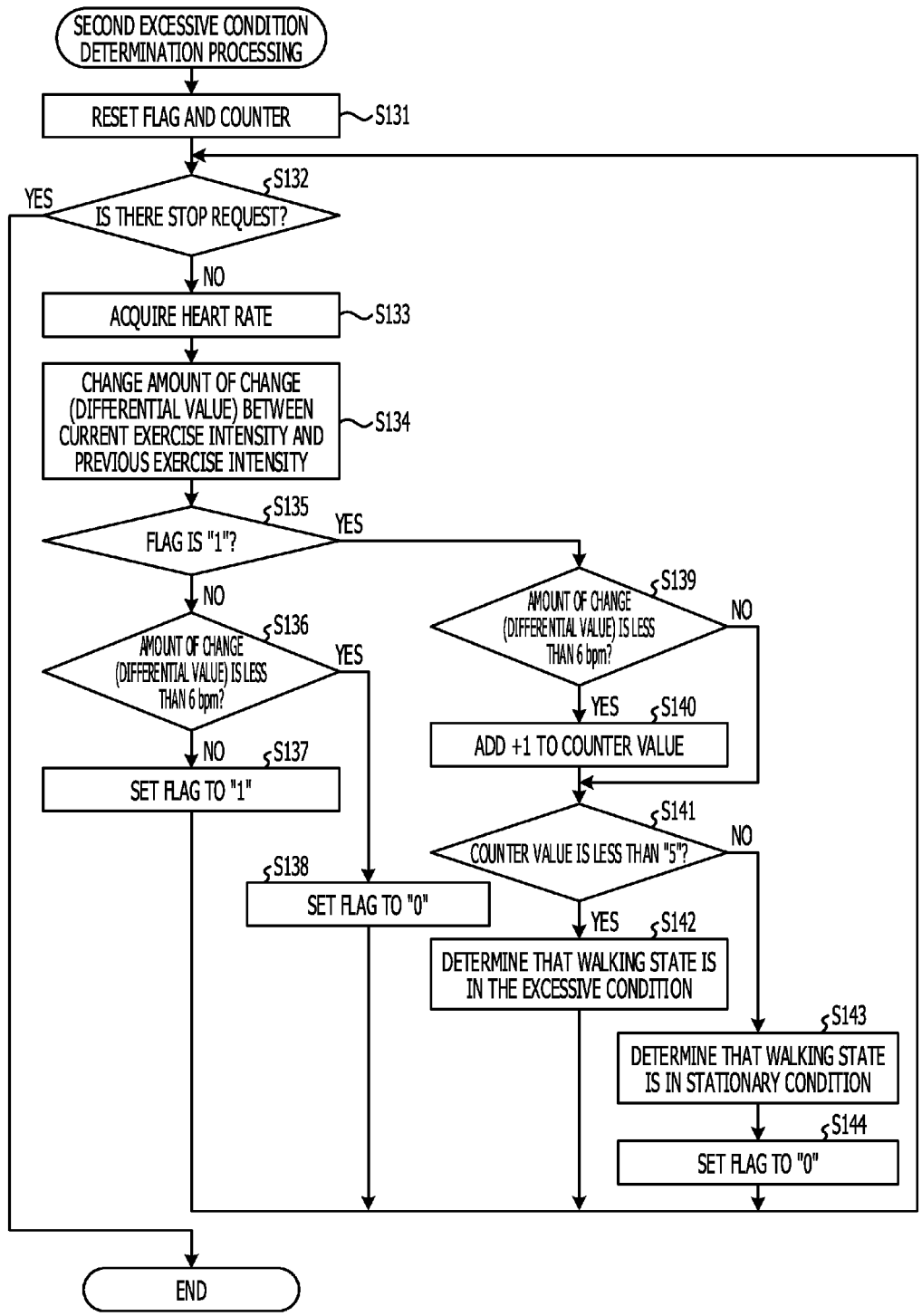
FIG. 15 is a flowchart illustrating an example of processing operations of a subprocessor of a portable terminal concerned with second excessive condition determination processing of a fourth embodiment.

The same configurations as the portable terminal 1 of the first embodiment are denoted by the same reference characters, and the descriptions of the overlapping configurations and operations will be omitted. FIG. 15 is a flowchart illustrating an example of processing operations of the subprocessor 22 of the portable terminal 1 concerned with second excessive condition determination processing. The second excessive condition determination processing illustrated in FIG. 15 is processing in which it is determined, on the basis of the elapsed time from the occurrence of a change in heart rate, whether the walking state of the subject is in the excessive condition.

The arithmetic processing unit 34 illustrated in FIG. 15 resets a flag and a counter (step S131), and determines whether a stop request of the application 28A has been detected (step S132). If a stop request of the application 28A has been detected (affirmative in step S132), the arithmetic processing unit 34 terminates the processing operations of FIG. 15. If a stop request of the application 28A has not been detected (negative in step S132), the arithmetic processing unit 34 acquires the heart rate of the subject through the millimeter wave sensor 25 (step S133) and calculates the amount of change (differential value) between the previous heart rate and the current heart rate (step S134).

After the amount of change (differential value) between the previous heart rate and the current heart rate has been calculated, the arithmetic processing unit 34 determines whether the flag is "1" (step S135). If the flag is not "1" (negative step S135), the arithmetic processing unit 34 determines whether the amount of change (differential value) between the previous heart rate and the current heart rate is less than 6 bpm (step S136). If the amount of change (differential value) in heart rate is not less than 6 bpm (negative in step S136), the arithmetic processing unit 34 sets the flag to "1" (step S137) and proceeds to step S132.

If the amount of change (differential value) in heart rate is less than 6 bpm (affirmative in step S136), the arithmetic processing unit 34 sets the flag to "0" (step S138) and proceeds to step S132. Otherwise, if the flag is "1" (affirmative step S135), the arithmetic processing unit 34 determines whether the amount of change (differential value) in heart rate is less than 6 bpm (step S139). If the amount of change (differential value) in heart rate is less than 6 bpm (affirmative in step S139), the arithmetic processing unit 34 adds +1 to the count value (step S140), and then determines whether the count value is less than "5" (step S141). Note that the count value is not limited to "5" and may be changed suitably.

If the count value is less than "5" (affirmative in step S141), the arithmetic processing unit 34 determines that the heart rate has not stabilized after the occurrence of a change in heartbeat, and determines that the walking state of the subject is in the excessive condition (step S142) and proceeds to step S132. If the amount of change (differential value) in heart rate is not less than 6 bpm (negative in step S139), the arithmetic processing unit 34 proceeds to step S141 in order to determine whether the count value is less than "5".

If the count value is not less than "5" (negative in step S141), the arithmetic processing unit 34 determines that the heart rate has stabilized after the occurrence of a change in heartbeat, and determines that the walking state of the subject is in the stationary condition (step S143) and sets the flag to "0" (step S144). Then, the arithmetic processing unit 34 proceeds to step S132 in order to determine whether a stop request has been detected.

The arithmetic processing unit 34 of the fourth embodiment sets the flag to "1" when the amount of change (differential value) between the heart rates has become 6 bpm or more, and then counts the number of times the amount of change (differential value) between the heart rates is less than 6 bpm. If the counted number of times the amount of change (differential value) between the heart rates is less than 6 bpm is less than 5, the arithmetic processing unit 34 determines that the heart rate has not stabilized after the occurrence of a change in heartbeat, and determines that the walking state of the subject is in the excessive condition. As a result, the arithmetic processing unit 34 may acquire an accurate exercise intensity by using the millimeter wave sensor 25 if the walking state is in the excessive condition.

If the counted number of times the amount of change (differential value) in heart rate is less than 6 bpm is not less than 5, the arithmetic processing unit 34 determines that the heart rate has stabilized after the occurrence of a change in heartbeat, and determines that the walking state of the subject is in the stationary condition and sets the flag to "0". As a result, when the walking state is in the stationary condition, the arithmetic processing unit 34 stops the millimeter wave sensor 25 and uses the acceleration sensor 24. Then, the arithmetic processing unit 34 acquires an exercise intensity by using the acceleration sensor 24, and it is possible to reduce the power consumption of the entirety of the portable terminal by an amount of power corresponding to the stopped millimeter wave sensor 25.

When it is determined that the walking state is in the excessive condition, the arithmetic processing unit 34 of the fourth embodiment counts the states where the amount of change (differential value) in heart rate is less than 6 bpm, and acquires an exercise intensity by using the millimeter wave sensor 25 until the number of counts exceeds a predetermined number of times. However, the heart rate rather than the amount of change (differential value) in heart rate may be monitored, and the millimeter wave sensor 25 may be used from the occurrence of a change in heartbeat at start of walking to a time point at which the heart rate has stabilized.

Also, it may be determined whether a predetermined period has elapsed since a time at which it was determined that the walking state at start of walking was in the excessive condition, and the exercise intensity may be acquired by using a millimeter wave sensor until the predetermined time has elapsed. In this case, the millimeter wave sensor 25 is used until a certain period has elapsed, and, after the elapse of the certain period, the millimeter wave sensor 25 is stopped and the acceleration sensor 24 is used.

Note that although the portable terminal 1, such as a smartphone, has been illustrated in each of the above embodiments, portable terminals such as portable game terminals, tablet terminals, portable terminals that do not have communication functions, for example, may be used.

Also, although, in the above embodiments, the acceleration threshold, the heart rate threshold, and the angular velocity threshold have been illustrated, these thresholds may be suitably changed depending on age, for example.

Also, components of each unit illustrated in the drawings are not to be physically configured as illustrated in the drawings. That is, the specific forms of distribution and integration of units are not limited to those illustrated in the drawings, and they may be in whole or in part configured in such a manner as to be functionally and physically distributed and integrated in arbitrary units depending on various loads and usage situations.

Furthermore, various processing functions performed with devices may be in whole or in part performed on a microcomputer, such as a central processing unit (CPU) or a micro processing unit (MPU). It is to be understood that various processing functions may be in whole or in part performed on programs that are analyzed and executed by a CPU (or a microcomputer such as an MPU or MCU) or on hardware using wired logic.

Figure 16:
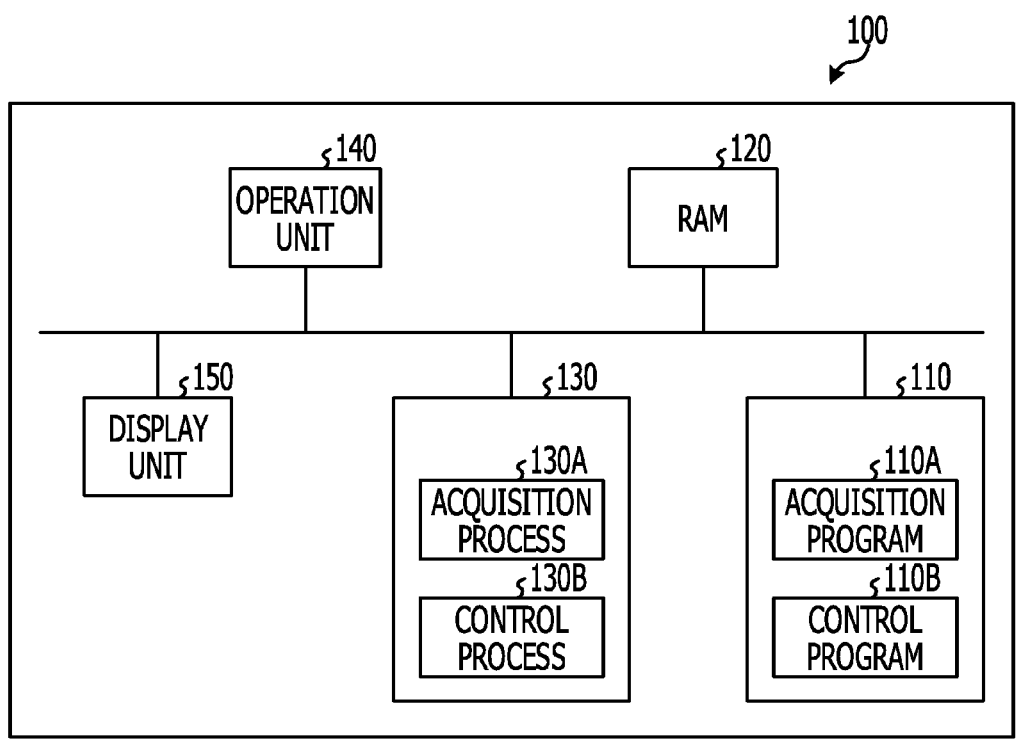
FIG. 16 is an explanatory diagram illustrating a portable electronic device for executing an exercise determination program.

By the way, various kinds of processing described in this embodiment may be implemented by executing programs provided in advance by using an electronic device. Accordingly, an example of a portable electronic device for executing programs having the same functions as the above embodiment will be described below. FIG. 16 is an explanatory diagram illustrating a portable electronic device for executing an exercise determination program.

A portable electronic device 100 for executing an exercise determination program illustrated in FIG. 16 includes a ROM 110, a RAM 120, a processor 130, an operation unit 140, and a display unit 150. The portable electronic device 100 also has an acceleration sensor and a millimeter wave sensor, which are not illustrated.

An exercise determination program that exhibits the same functions as the above embodiment is stored in advance in the ROM 110. Note that the exercise determination program may be recorded on a recording medium that is readable by a drive (not illustrated), rather than in the ROM 110. As a recording medium, for example, a portable recording medium such as a CD-ROM, a DVD disk, a USB memory, or an SD card, a semiconductor memory, such as a flash memory, may be used. As the exercise determination program, as illustrated in FIG. 16, an acquisition program 110A and a control program 110B are used. Note that the programs 110A and 110B may be unified or distributed suitably.

Then, the processor 130 reads these programs 110A and 110B from the ROM 110 and executes each of the read programs. Then, the processor 130 causes the programs 110A and 110B to function as an acquisition process 130A and a controlling process 130B as illustrated in FIG. 16.

The processor 130 acquires a detection value from an acceleration sensor, and controls starting or stopping of a heart rate sensor depending on the acquired detection value. As a result, when the walking state is in the stationary condition, the heart rate sensor is stopped and the acceleration sensor is used. Thus, the power consumption of the entirety of the portable electronic device 100 may be reduced. When the walking state is in the excessive condition, the heart rate sensor is used. Thus, an accurate exercise state may be determined using a heart rate.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An exercise determination method, comprising acquiring a detection value from an acceleration sensor;
controlling, by a processor, after a heart rate sensor has been started, restarting or stopping the heart rate sensor depending on the acquired detection value of the acceleration sensor, and
switching between calculating an exercise intensity based on a detection value of the acceleration sensor and calculating an exercise intensity based on a detection value of the heart rate sensor, depending on a difference between the first detection value and the second detection value
wherein
the controlling includes controlling starting or stopping of the heart rate sensor depending on a difference between a first detection value acquired from the acceleration sensor and a second detection value acquired from the acceleration sensor before the first detection value.

2. An electronic device, comprising:
an acceleration sensor;
a memory; and
a processor coupled to the memory, configured to:
acquire a detection value from the acceleration sensor,
after a heart rate sensor has been started, control restarting or stopping the heart rate sensor depending on the acquired detection value of the acceleration sensor, and
depending on a difference between the first detection value and the second detection value, switch between calculating an exercise intensity based on a detection value of the acceleration sensor and calculating an exercise intensity based on a detection value of the heart rate sensor,
wherein the processor is configured to control starting or stopping of the heart rate sensor depending on a difference between a first detection value acquired from the acceleration sensor and a second detection value acquired from the acceleration sensor before the first detection value.

3. A non-transitory, computer readable medium storing a program that, when executed by a processor, causes the processor to perform operations comprising:
acquiring a detection value from an acceleration sensor;
controlling, after a heart rate sensor has been started, restarting or stopping the heart rate sensor depending on the acquired detection value of the acceleration sensor; and
switching between calculating an exercise intensity based on a detection value of the acceleration sensor and calculating an exercise intensity based on a detection value of the heart rate sensor, depending on a difference between the first detection value and the second detection value,
wherein the controlling includes controlling starting or stopping of the heart rate sensor depending on a difference between a first detection value acquired from the acceleration sensor and a second detection value acquired from the acceleration sensor before the first detection value.

4. The exercise determination method according to claim 1, wherein the controller starts and stops the heart rate sensor by starting and stopping the power being supplied to the heart rate sensor.

5. The non-transitory, computer readable medium of claim 3, wherein controlling the starting and stopping of the heart rate sensor comprises starting and stopping the power being supplied to the heart rate sensor.

6. The exercise determination method according to claim 1, wherein the controller starts and stops the heart rate sensor depending on the whether an amount of change of a signal of the heart rate sensor is less than a predetermined value or an amount of change of the acquired detection value is less than a second predetermined value.

7. The non-transitory, computer readable medium of claim 3, wherein the heart rate sensor is started or stopped based on the whether an amount of change of a signal of the heart rate sensor is less than a predetermined value or an amount of change of the acquired detection value is less than a second predetermined value.

* * * * *